United States Patent [19]

Peters et al.

[11] Patent Number: 5,549,619
[45] Date of Patent: Aug. 27, 1996

[54] MEDICAL/SURGICAL DEVICES

[75] Inventors: Joseph L. Peters, Ware; James W. Kerr, Gravesend, both of England

[73] Assignee: Clinical Product Development Limited, Kent, England

[21] Appl. No.: 157,135
[22] PCT Filed: Jun. 4, 1992
[86] PCT No.: PCT/GB92/01005
§ 371 Date: Dec. 14, 1993
§ 102(e) Date: Dec. 14, 1993
[87] PCT Pub. No.: WO92/22041
PCT Pub. Date: Dec. 10, 1992

[30] Foreign Application Priority Data

Jun. 4, 1991 [GB] United Kingdom ............ 9111972

[51] Int. Cl.⁶ ..................................... A61B 17/00
[52] U.S. Cl. ................ 606/151; 606/213; 606/215; 606/216
[58] Field of Search .................... 606/151, 157, 606/158, 213, 215, 216, 218, 220

[56] References Cited

U.S. PATENT DOCUMENTS

| | | | |
|---|---|---|---|
| 3,339,247 | 9/1967 | Geisinger | 606/151 |
| 3,570,497 | 3/1971 | Lemole . | |
| 3,577,601 | 5/1971 | Mariani et al. | 606/151 |
| 3,926,193 | 12/1975 | Hasson | 606/218 |
| 4,069,825 | 1/1978 | Akiyama | 606/158 |
| 4,519,392 | 5/1985 | Lingua | 606/151 |
| 4,669,473 | 6/1987 | Richards et al. | 606/215 |
| 4,730,615 | 3/1988 | Sutherland et al. | 606/215 |
| 4,732,151 | 3/1988 | Jones . | |
| 4,821,878 | 4/1989 | Jones . | |
| 4,832,026 | 5/1989 | Jones . | |
| 4,834,098 | 5/1989 | Jones . | |
| 4,865,032 | 9/1989 | Jones . | |
| 4,874,370 | 10/1989 | Heimerl et al. . | |
| 4,950,284 | 8/1990 | Green et al. | 606/151 |
| 5,123,913 | 6/1992 | Wilk et al. | 606/151 |
| 5,304,188 | 4/1994 | Marogil | 606/157 |

FOREIGN PATENT DOCUMENTS 972731 10/1964 United Kingdom ............ 606/158

*Primary Examiner*—Gary Jackson
*Assistant Examiner*—Jeffrey A. Schmidt
*Attorney, Agent, or Firm*—Watson Cole Stevens Davis, P.L.L.C.

[57] ABSTRACT

A securing device for medical and surgical use has two parts which may be separate or integrally connected, one part including an eye (3) with a latching pawl (4) and the other part including a flexible strip (1) with ratchet teeth (2) so that the strip can be advanced through the eye to adjust the effective length of the flexible strip, but is locked against reverse movement. In one embodiment the parts are integral and a needle (7) is attached to the free end of the flexible strip, the device being a surgical suture. In another embodiment the parts are separate and are adapted to engage respective body parts of a patient which are to be held together by the device.

6 Claims, 3 Drawing Sheets

MEDICAL/SURGICAL DEVICES

BACKGROUND OF THE INVENTION

The invention is concerned with devices for medical and especially, but not necessarily exclusively, surgical applications. More particularly, the invention relates to such a device for attachment to a patient either for connecting together body parts, e.g., for closing wounds produced during surgical procedures, or for securing an external component, such as a cannula, to a body part to prevent accidental displacement.

The most common technique employed for wound closure during surgical operations is that of stitching using either nylon or other plastic thread or stainless steel wire where greater strength is required. Stitching is often complicated by the need to tie knots which must be reliable and not slip, and this frequently prolongs the time taken to complete an operation, thereby adding to the stress and trauma imparted upon the patient. Furthermore, it is sometimes necessary to apply a certain tension between body parts being connected together, which is difficult to achieve when conventional stitching methods are relied upon, whereby substantial skill is required on the part of the surgeon.

In U.S. Pat. No. 4,874,370 there is disclosed a securing strip for encircling a section of intestine to hold it onto a tubular adaptor inserted into the section of intestine. The securing strip has teeth and a channel portion at one end with complementary depressions so that the strip can be formed into a loop and tightened, the other end of the tie having a ring tab to assist tightening. This strip functions like a well known cable tie for holding together bundles of electric cables and it does not provide an answer to the drawbacks mentioned above.

SUMMARY OF THE INVENTION

The present invention addresses these drawbacks and as a solution it proposes a medical securing device comprising an elongate first part in the form of a flexible strip having a free end and having ratchet means provided therealong, and a second part including an eye for the free end to be passed therethrough, the eye including latching means arranged to cooperate with the ratchet means to permit forward movement of the strip through the eye but to retain the strip securely against reverse movement through the eye, thereby to enable the effective length of the first part to be adjusted, characterised in that the first part has fixed thereto means for use in attaching the first part to a body part of a patient and/or for connecting another external member thereto.

According to a first embodiment of the securing device adapted for wound closure, a needle (or stylet) is fixed to the free end of the flexible strip, and the eye is integrally connected to the other end of the strip. The needle is used to thread the flexible strip through, e.g., tissue segments to be sutured, and is then passed through the eye to lead the free end of the strip therethrough, whereby the strip is formed into a loop. The strip is pulled through the eye until the required tension is obtained in the loop and thereafter the needle, and possibly the excess length of strip protruding through the eye, is cut away. Such an embodiment facilitates the application of reliable sutures and also allows accurate control over the suture tension. It may be applied with considerable advantage in the closure of abdominal wounds, for closing together the sternum and in other similar procedures.

In accordance with another embodiment of the invention, the device comprises first and second parts which are separate and adapted for engagement with respective body parts or segments. When the two parts of the device have been engaged with the respective segments the flexible strip can be advanced through the eye to reduce the effective length of the strip and put the strip under tension. A device of this form could be used to advantage, for example, in repairing or rebuilding a ruptured organ, such as a liver, by being applied to span a split in the organ and to hold the split closed so that it may heal together. Another possible application may be in mending fractured bones with the device being fitted to the bone to span the fracture and being tightened to hold the bone segments together for healing. From the foregoing it will be appreciated that the two parts of the device may be provided with various means, formed integrally or fastened thereto, for connecting them to body parts as desired by the particular surgical application to which the device is to be put, such as studs for socketing into bone, bars or plates for attachment to organs, muscle tissue etc., or elements of other configurations.

According to another embodiment of the invention the eye is integral with the end of the flexible strip opposite the free end, and at a position intermediate its ends the strip has means integral therewith and projecting laterally therefrom for engagement with an external member, e.g. a cannula in which case the integral means may comprise a collar or C-shaped clip. This embodiment may be applied around a limb, e.g. the arm of a patient, under light tension, and serve to hold a cannula or other external element fitted to the patient against main unintentional detachment or displacement.

BRIEF DESCRIPTION OF THE DRAWINGS

A better understanding of the invention will be had from the following detailed description of some embodiments, reference being made to the accompanying drawings, in which.

DETAILED DESCRIPTION OF THE PREFERRED EMBODIMENTS

Figure 1:
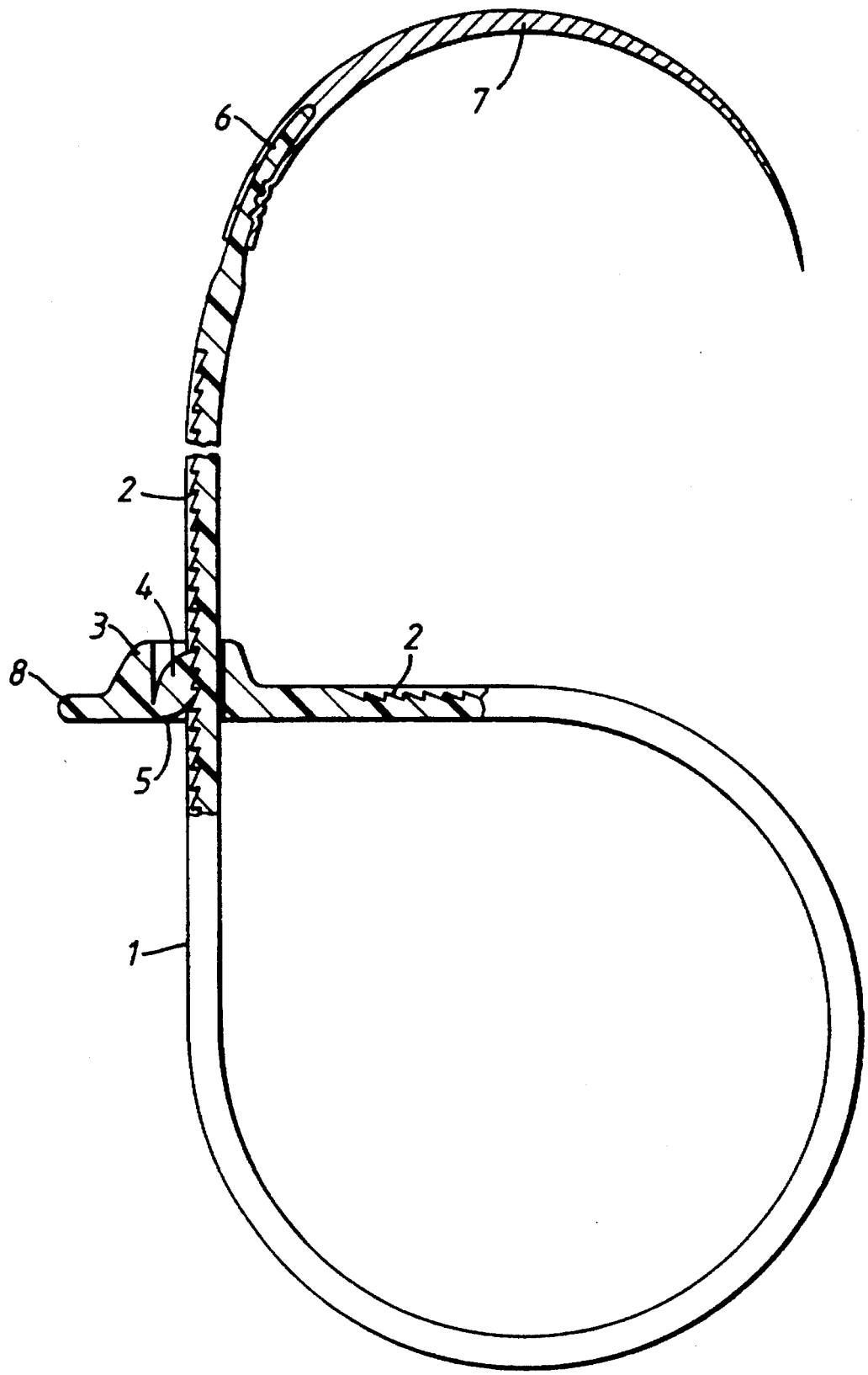
FIG. 1 is a schematic longitudinal cross-section through a suturing device according to the invention.

The surgical suture device shown in FIG. 1 comprises an integrally moulded member comprising a flexible strip 1 formed with a series of ratchet teeth 2 extending along a major part of its length (for convenience not all of the teeth are shown), and a generally rectangular eye 3 integral with a trailing end of the strip 1 and incorporating an integral latching finger or pawl 4 for engagement with the teeth 2 as shown to lock the strip 1 against reverse movement through the eye while permitting substantially unopposed forward movement of the strip, the pawl 4 being hinged at 5 to permit such forward movement. As so far described the moulded member is of a construction known per se, such members being commonly known as cable ties and being used to hold together bundles of electric cables and for other such purposes.

In the device of FIG. 1, the moulded member is provided at its free end with an integral tongue 6 onto which is fixed a tubular stylet or needle 7. As shown the needle is curved, but a straight needle is also possible. The needle is fastened securely to the tongue by crimping, or by any other convenient method, such as moulding the strip onto the needle.

Prior to use, the strip 1 is generally ly rally straight and it does not extend through the eye 3. The needle 6 is used to lead the strip 1 through the tissue segments to be sutured, and is then passed through the eye 3 to form the strip 1 into a closed loop, as seen in FIG. 1. The strip is advanced through the eye until the required tension is obtained in the loop. The needle, and the excess strip protruding from the eye are then cut off and discarded. To facilitate the closing and tightening of the loop, the eye 3 is provided with means to enable it to be gripped in the jaws of a pair of forceps. As shown this means is constituted by a lip or flange 8 at the side of the eye opposite that side to which the strip 1 is attached, and the surfaces of this lip may be knurled or serrated to enhance the gripping action of the forceps, and/or the lip may have a hole therethrough so that it can be easily held with small-nosed medical forceps. Of course the eye may be provided with alternative formations to enable it to be gripped, e.g., a recess in the side wall defining an edge with which the forceps jaws may be engaged, or an elongate filament, say 2–3 cms long, forming a tail which may be twisted onto small remote controlled surgical tools as used in non-invasive micro-surgery.

The suture device shown in FIG. 1, is quick and simple to apply and allows easy control of the suture tension. The moulded member forming the strip 1 and eye 3 may be made from medical grade nylon, or perhaps a biodegradable polymer so that it will in time become absorbed in the body.

Figure 2:
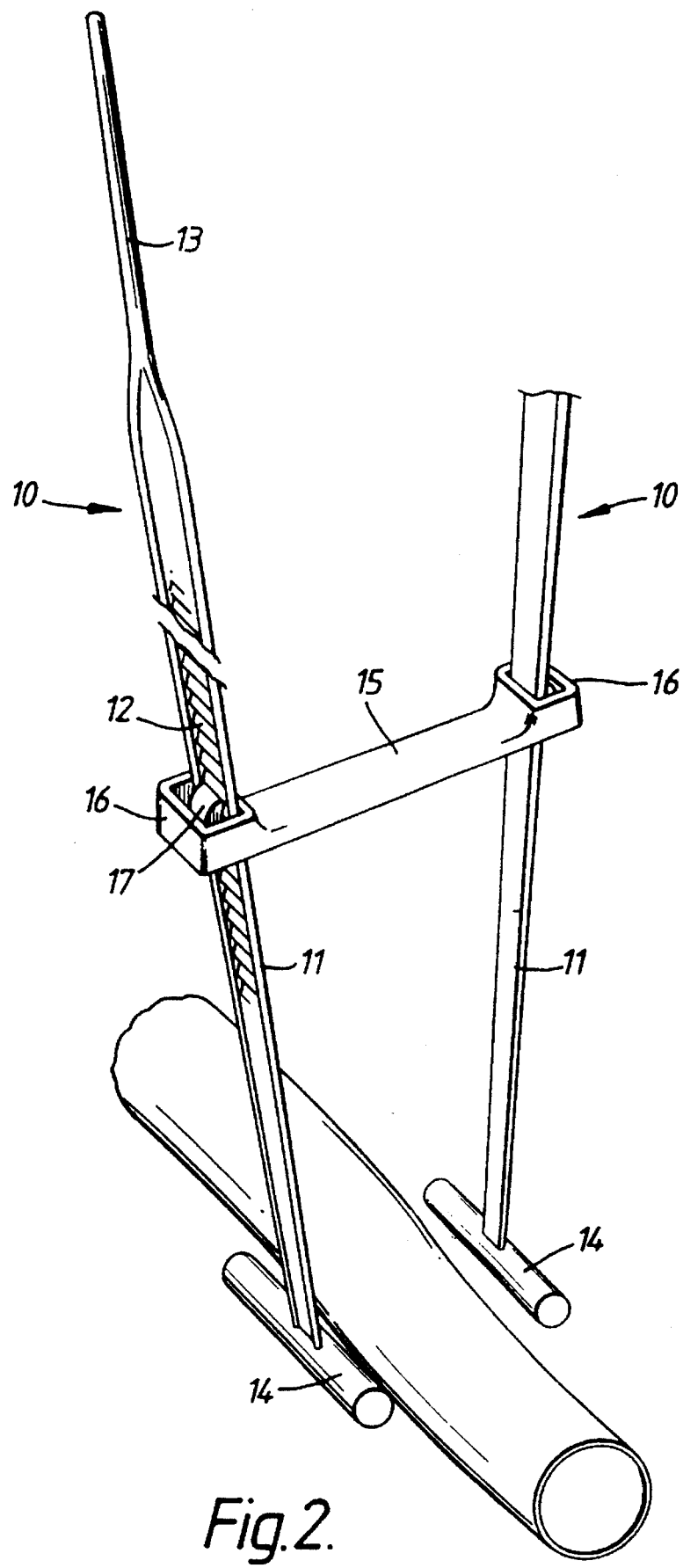
FIG. 2 is a perspective view showing a suture device for a female incontinence sling procedure.
Figure 3:
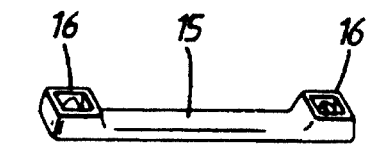
FIG. 3 is a perspective view showing another embodiment of a suture device for a female incontinence sling procedure.
Figure 3:
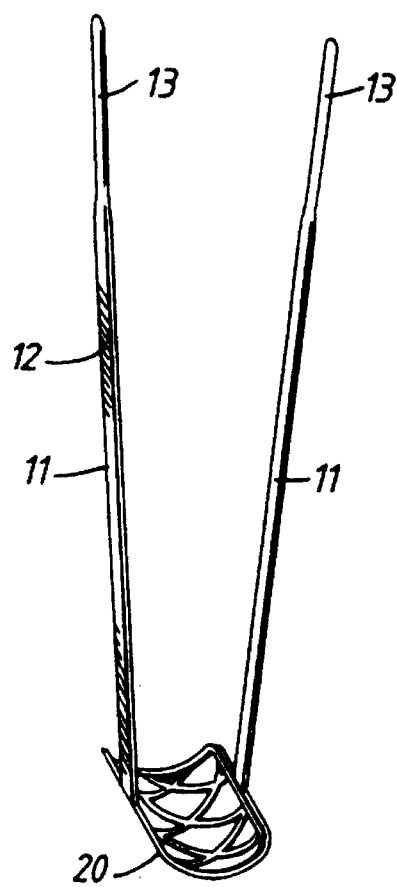

In FIG. 2 there is illustrated a suture device for a female incontinence sling procedure. The device is formed in three separate parts, the first two parts 10 being essentially identical ties and each taking the form of a flexible strip 11 with ratchet teeth 12 along its length, an integral tapered tip 13 at the leading end of the strip and a transverse anchoring bar 14 integral with the trailing end of the strip. The other part of the device consists of a relatively stiff bar 15 having an integral eye 16 at each end. The eyes are equipped with latching pawls 17, in the same manner as the eye 3 in the FIG. 1 suture device, so that the strips 11 of the respective parts 10 may be inserted through the eyes 16 and will become automatically locked against reverse movement due to the engagement of the latching pawls 17 with the ratchet teeth 12. All three parts of the device can be moulded from medical grade nylon.

In application of the device the two parts are introduced through the vagina of the patient and are directed upwardly through the small incisions so that the anchorage bars 14 become engaged in tissue on either side of the urethra. The cross bar 15 is implanted subcutaneously at a lower abdominal region so that the tips 13 can be fed through the respective eyes 16. The tips 13 and flexible strips 11 attached thereto are pulled through the eyes to adjust the effective length of the strips 11 between the anchorage bars 14 and the cross bar 15, and thereby the tension in the strips 11, so that the urethra is lifted and normal constitution of the bladder neck anatomy is restored. The latching system provided by the pawl and ratchet teeth enables accurate adjustment of the length and tension of the tie strips. The leading ends of the strips above the cross bar 15 can be cut off and discarded after the suture device has been fitted and adjusted.

In addition to making such sling procedures easier and quicker to perform, the suture device of the invention has the added benefit that if further laxity should occur, the sling device can be adjusted by tightening up the ties 10 by advancing them through the eyes.

Figure 4:
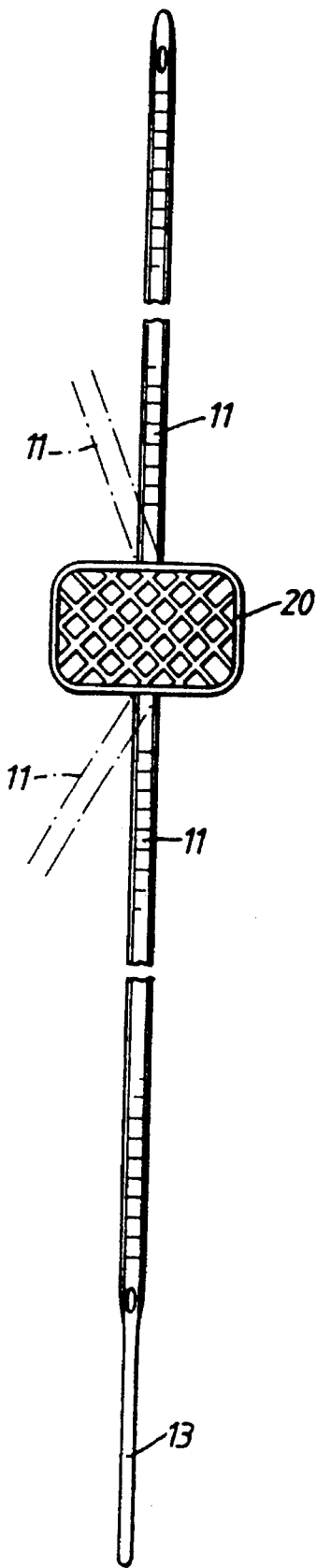
FIG. 4 shows a plan view of the sling member of the device of FIG. 3.

If preferred a web of Dacron or net could be arranged to extend between the anchorage bars 14 and pass beneath the urethra for directly supporting it from below. Shown in FIG. 4, is an alternative form of sling procedure suture in which such a web or sling is integral with the tie parts. Thus, in place of the bars 14, the two flexible strips 11 are fastened to opposite sides of a web 20 which has a mesh-like structure. In all other respects the device is as described above with reference to FIG. 2. Although the strips 11 are shown to be in longitudinal alignment, they may be arranged at an angle e.g. as depicted in broken line in FIG. 4, so that the web will be better oriented for supporting the urethra.

It will be appreciated that the invention is not restricted to the particular embodiments described above and the novel principles involved are applicable to a wide variety of different devices adapted for differing medical or surgical duties. However, the invention is especially advantageous where a suture with an effective length which can be gradually reduced, e.g. to adjust the tension, is desirable.

We claim:

1. A surgical suture device comprising an elongate flexible strip having ratchet means provided therealong, a complete annular eye integral with one end of the strip, a needle fastened to the other end of the strip, the needle being insertable through the eye to form the strip into a loop and the eye having latching means arranged to permit forward movement of the strip through the eye to reduce the size of the loop but to restrain the strip securely against reverse movement through the eye, wherein:

the eye defines a lengthwise extension of the strip whereby a strip portion extending through the eye is substantially perpendicular to the strip end portion attached to the eye; and the eye has integral, one piece flattened holding means projecting therefrom in a direction away from the strip for engagement by a gripping tool; and the needle has a tubular trailing end in which is fixed a tongue integral with said other end of the strip.

2. A surgical suture device according to claim 1, wherein the tongue is fixed in the needle by crimping.

3. A surgical suture device according to claim 2, wherein the holding means comprises a flange.

4. A surgical suture device comprising an elongate flexible strip having ratchet means provided therealong, an eye integral with one end of the strip, a needle fastened to another end of the strip, the needle being insertable through the eye to form the strip into a loop and the eye having latching means arranged to permit forward movement of the strip through the eye to reduce the size of the loop but to restrain the strip securely against reverse movement through the eye, wherein:

the eye defines a lengthwise extension of the strip whereby a strip portion extending through the eye is substantially perpendicular to the strip end portion attached to the eye;

the eye has an integral flange projecting therefrom in a direction away from the strip;

the flange has a hole therein for cooperation with a gripping tool; and the needle has a tubular trailing end in which is fixed a tongue integral, one piece with said other end of the strip.

5. A medical securing device for attachment to a patient comprising a pair of elongate first parts, each in the form of a flexible strip having a free end, a member integrally connected in one piece to another end for securing the flexible strip to a body part of a patient, and having ratchet means provided therealong, and a separate second part including two eyes for the free ends of the respective flexible strips to be passed therethrough, each said eye including latching means arranged to cooperate with the ratchet means to permit forward movement of the strip through the eye but to retain the strip securely against reverse movement through the eye, thereby to enable the effective length of the respective first part to be adjusted, and wherein the first parts are separate and each said member comprises an elongated bar having a longitudinal axis extending transversely of the flexible strip.

6. A medical securing device for attachment to a patient comprising a pair of elongate first parts, each in the form of a flexible strip having a free end, a member integrally connected in one piece to another end for securing the flexible strip to a body part of a patient, and having ratchet means provided therealong, and a separate second part including two eyes for the free ends of the respective flexible strips to be passed therethrough, each said eye including latching means arranged to cooperate with the ratchet means to permit forward movement of the strip through the eye but to retain the strip securely against reverse movement through the eye, thereby to enable the effective length of the respective first part to be adjusted, and wherein the respective flexible strips are connected to a common member forming a sling means, the sling means comprising a generally rectangular mesh having the flexible strips integrally connected in one piece with opposite sides thereof.

* * * * *